(12) United States Patent
Gaillard et al.

(10) Patent No.: US 7,598,723 B2
(45) Date of Patent: Oct. 6, 2009

(54) METHOD AND APPARATUS FOR DETECTING RESONANCE IN ELECTROSTATICALLY DRIVEN ELEMENTS

(75) Inventors: Jay Gaillard, Clemson, SC (US); Razvan Marian Ciocan, Central, SC (US); Malcolm Skove, Central, SC (US); Apparao M. Rao, Anderson, SC (US)

(73) Assignee: Clemson University

( * ) Notice: Subject to any disclaimer, the term of this patent is extended or adjusted under 35 U.S.C. 154(b) by 0 days.

(21) Appl. No.: 11/354,268

(22) Filed: Feb. 14, 2006

(65) Prior Publication Data

US 2006/0255790 A1   Nov. 16, 2006

Related U.S. Application Data

(60) Provisional application No. 60/652,754, filed on Feb. 14, 2005, provisional application No. 60/708,149, filed on Aug. 15, 2005.

(51) Int. Cl.
*G01R 23/14* (2006.01)
*G01P 15/097* (2006.01)
*G01R 27/26* (2006.01)

(52) U.S. Cl. .................. 324/76.42; 324/633; 324/76.41; 324/76.11

(58) Field of Classification Search .............. 324/76.15, 324/76.42, 633, 652, 668, 675, 682, 708
See application file for complete search history.

(56) References Cited

U.S. PATENT DOCUMENTS

| | | | |
|---|---|---|---|
| 4,805,456 A * | 2/1989 | Howe et al. | 73/514.18 |
| 5,258,923 A * | 11/1993 | Imam et al. | 702/36 |
| 5,266,896 A * | 11/1993 | Rugar et al. | 324/307 |
| 5,306,412 A * | 4/1994 | Whitehouse et al. | 204/452 |
| 5,442,288 A * | 8/1995 | Fenn et al. | 324/244 |
| 5,719,324 A * | 2/1998 | Thundat et al. | 73/24.01 |
| RE36,603 E * | 3/2000 | Pohl et al. | 365/151 |
| 6,249,000 B1 * | 6/2001 | Muramatsu et al. | 250/306 |
| 6,368,275 B1 * | 4/2002 | Sliwa et al. | 600/437 |

(Continued)

OTHER PUBLICATIONS

Article—*A New Tunneling-Based Sensor for Inertial Rotation Rate Measurements*, Kubena et al., Journal of Microelectromechanical Systems, vol. 8, No. 4, Dec. 1999, pp. 439-447.

(Continued)

*Primary Examiner*—Timothy J Dole
*Assistant Examiner*—John Zhu
(74) *Attorney, Agent, or Firm*—Dority & Manning, P.A.

(57) ABSTRACT

A method and system is disclosed that can be used to directly detect and analyze an electric signal electrostatically induced a semi-conductive or conductive element at resonance. Through detection of the changes in the characteristics of the signal from the element, the disclosed devices can detect, for instance, presence of chemical/biological species in a sample or measure physical parameters of a sample such as pressure/acceleration, magnetic force, temperature, and/or extremely small masses. The disclosed systems include one or more micro- or nano-sized elements. Through modulation of an electric charge on a counter-electrode that is located at a pre-determined distance from the element, a modulating charge can be induced upon the element. Resonance can be directly detected via electronic monitoring of the induced signal for the higher harmonics of the natural resonant frequency.

34 Claims, 11 Drawing Sheets

U.S. PATENT DOCUMENTS

| | | | | |
|---|---|---|---|---|
| 6,444,927 | B1* | 9/2002 | Korpi | 177/210 FP |
| 6,555,945 | B1* | 4/2003 | Baughman et al. | 310/300 |
| 6,593,731 | B1 | 7/2003 | Roukes et al. | |
| 6,642,129 | B2* | 11/2003 | Liu et al. | 438/496 |
| 6,668,627 | B2* | 12/2003 | Lange et al. | 73/105 |
| 6,676,813 | B1 | 1/2004 | Pelekhov et al. | |
| 6,722,200 | B2 | 4/2004 | Roukes et al. | |
| 6,734,425 | B2* | 5/2004 | Hantschel et al. | 250/306 |
| 6,823,724 | B1* | 11/2004 | Kobayashi et al. | 73/105 |
| 6,845,655 | B2* | 1/2005 | van der Weide et al. | 73/105 |
| 6,879,012 | B2 | 4/2005 | Tang et al. | |
| 6,894,272 | B2* | 5/2005 | Kranz et al. | 250/234 |
| 6,910,382 | B2 | 6/2005 | Tang et al. | |
| 6,935,167 | B1* | 8/2005 | Sahin et al. | 73/105 |
| 7,068,027 | B1* | 6/2006 | Mastro et al. | 324/204 |
| 2006/0075836 | A1* | 4/2006 | Zribi et al. | 73/866.1 |
| 2006/0150719 | A1* | 7/2006 | Reinstadtler et al. | 73/105 |

OTHER PUBLICATIONS

Article—*Determination of the Bending Modulus of an Individual Multiwall Carbon Nanotube using an Electric Harmonic Detection of Resonance Technique*, Ciocan et al., Nano Letters, vol. 5, No. 12, 2005, pp. 2389-2393.

Article—*Mechanical properties of chemical vapor deposition-grown multiwalled carbon nanotubes*, Gaillard et al., Applied Physics Letters, vol. 86, 2005, pp. 233109-1-233109-3.

Paper from Technology Review—The Impact of Emerging Technologies: Demo: Sensing Success by David Rotman, Dec. 2005/Jan. 2006, 14 pages.

Poster from Clemson University entitled *Determination of Nanotube Density by Gradient Sedimentation* by Lu et al., prepared for the Sixth International Conference on the Science and Application of Nanotubes, 2005, Gothenburg, Sweden, Jun. 2005, 1 page.

\* cited by examiner

METHOD AND APPARATUS FOR DETECTING RESONANCE IN ELECTROSTATICALLY DRIVEN ELEMENTS

CROSS REFERENCE TO RELATED APPLICATIONS

This application claims benefit of Provisional Application Ser. No. 60/652,754, filed on Feb. 14, 2005 and claims benefit of Provisional Application Ser. No. 60/708,149 filed on Aug. 15, 2005.

FEDERALLY SPONSORED RESEARCH AND DEVELOPMENT

The United States Government may have rights in this invention pursuant to National Science Foundation Grant No. 2003863.

BACKGROUND OF THE INVENTION

The ability to build extremely small devices via recently discovered micro- and nano-fabrication processes has opened the door to the possibility of electromechanical machines and sensors of a size existing only in the realm of science fiction in previous generations. For instance, many methods now exist to build working microelectromechanical systems (MEMS) as well as even smaller nanoelectromechanical systems (NEMS). While the technology to build these devices is continuing to expand and grow, practical applications for such devices remain elusive. Problems currently faced by researchers in taking this final step often center around the challenges to be overcome in regard to communicating to the macroscopic world the mechanical motion and/or the electronic signals generated on the micro- or nano-sized scale. For instance, as the devices are so small, the capacitance of a signal junction can approach the unavoidable parasitic capacitance due to the existence of junctions between components of the device, as well as the resting capacitance of the device itself. As such, the devices can describe an extremely low signal to noise ratio, making the detection of an electrical signal very difficult, if not impossible.

Some of the primary mechanical elements being utilized in the development of MEMS and NEMS technology include micro- and nano-sized cantilevers, clamped beams, and the like. Such devices are often used in sensing or actuating technologies and are generally based upon the changes in a property of the cantilever or beam due to absorption or adsorption of a species at the surface or due to changes in the physical characteristics of a sample including, for instance, pressure/acceleration changes, magnetic force changes, temperature changes, and/or extremely small changes in mass. Detection of change in resonant frequency of a device is one particular mechanical property that has been used in many such regimes. Changes in the oscillating or resonant frequency of a micro- or nano-sized beam have generally been limited to determination through optical detection, e.g., analysis of the deflection properties of a laser directed at a reflecting surface of the cantilever, analysis and detection of changes in the resistivity of a piezoresistor integrated into the cantilever, or analysis of magnetically induced signals.

Difficulties exist with these detection methods, however. For instance, optical detection techniques require optical access to the cantilever as well as the utilization of relatively expensive laser technologies. Integration of a piezoresistor to a cantilever so as to detect changes in resistivity on the material can necessitate increase in size as well as cost of the apparatus. Also, the large magnetic fields required in magnetic systems can be difficult and expensive to establish.

Accordingly, there remains room for variation and improvement within the art.

SUMMARY OF THE INVENTION

In general, the present invention is directed to methods for detecting resonance in semi-conductive or conductive elements and devices that utilized the disclosed method. For instance, the method can include applying a signal to a counter electrode and thereby inducing an electrostatic force on an element that is in a non-contact arrangement with the counter electrode. In response to the electrostatic force, an electric signal can be generated at the element. At resonance, this signal will contain not only the fundamental mode of the applied signal, but will also contain the higher harmonics of the applied signal. Hence, the disclosed methods include examining this generated signal to ascertain the presence of the one or more of the higher harmonics of the applied signal in order to detect resonance in the element. For example, the generated signal can be examined to ascertain the presence of the second harmonic of the third harmonic of the applied signal.

In one particular embodiment, the frequency of the generated signal can be examined to determine the presence of higher harmonics of the applied signal. For instance, both the applied and generated signals can be fed to a signal processor such as a lock-in amplifier, and the frequencies of the signals can be examined for the presence of higher harmonics in the generated signal. If desired, the process can also include determination of the Quality factor of the generated signal.

The elements of the disclosed devices can be micro- or nano-sized elements. In general, the elements can be less than about 500 μm in length and less than about 50 μm in width. In one embodiment, the elements can be nano-sized. For example, the element can be less than about 500 nm in width, for example a single walled nanotube of 1 nm in diameter. In one embodiment, the element can include one or more carbon-based nanostructures. For instance, the element can include a carbon nanotube. The elements can also have any suitable geometry and orientation in the device. For example, the element can be a single-clamped cantilever or a double-clamped beam.

The spatial relationship between the counter electrode and the element can be such that the electrostatic force can be induced on the element. For instance, the element and the counter electrode can be in a parallel arrangement or a tip-to-tip arrangement. Beneficially, the two can be farther apart than thought possible in MEMS and NEMS systems of the past, due to the resonant detection regime described herein. For instance, a micro-sized system can have the two in parallel arrangement and between about 10 μm and about 20 μm apart, in one embodiment. And when considering a nano-sized element, one embodiment of the invention includes the element and the counter electrode located between about 10 nm and about 2 μm apart from one another.

The disclosed devices can include any device in which the direct electric detection of resonance in an element can be beneficial. For instance, the disclosed devices can include chemical sensors in which the resonant frequency of the element can change upon the interaction of the element with a chemical species. Accordingly, the element of the device can be monitored for a change in resonant frequency, for instance through application of a modulated signal to the counter electrode, and a detected change in resonant frequency can signal the presence of a species of interest. While the interaction of the element and the species can include contact, for instance adsorption of the species onto the element, this is not a requirement of the invention, and in other embodiments, the interaction need not include actual contact.

Other electrical devices encompassed by the present invention include atomic force microscopes, high Q-factor oscillators, switching devices, antennas, and the like.

BRIEF DESCRIPTION OF THE FIGURES

A full and enabling disclosure of the present invention, including the best mode thereof, to one of ordinary skill in the art, is set forth more particularly in the remainder of the specification, including reference to the accompanying figures in which.

Figure 1:
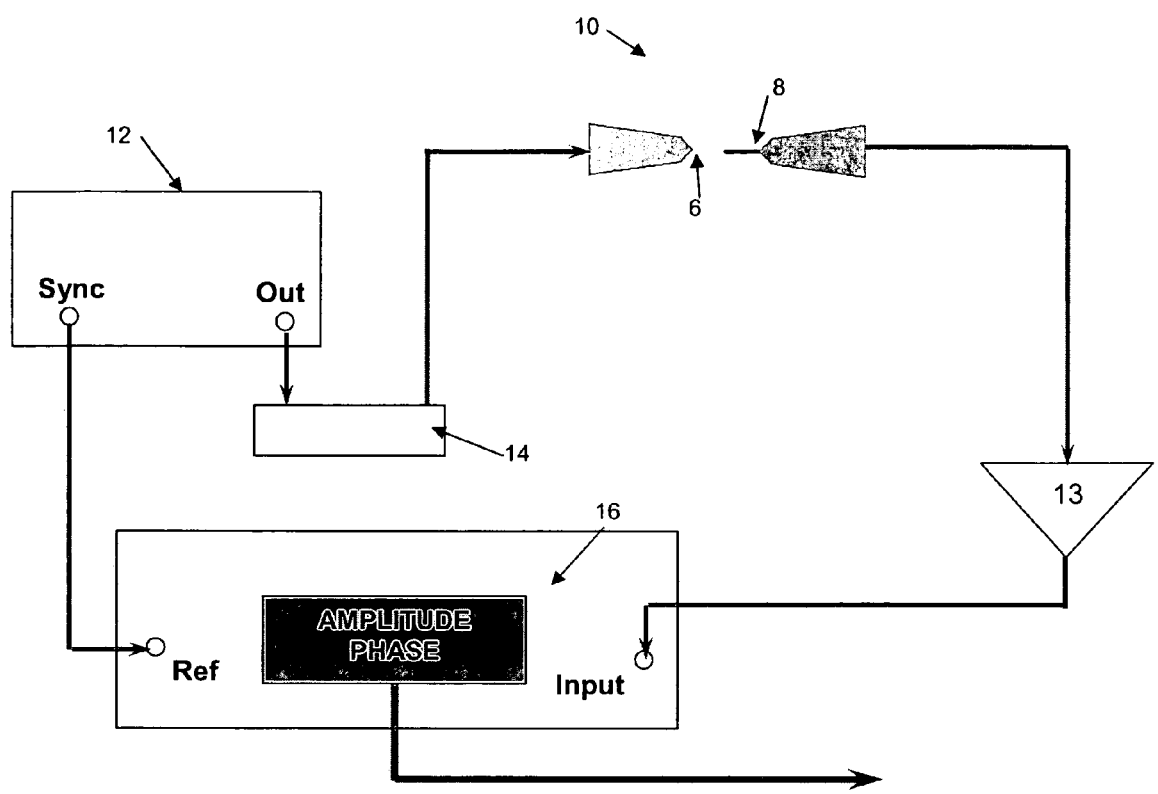
FIG. 1 is a schematic diagram of one embodiment of a system of present invention.

Repeat use of reference characters in the present specification and drawings is intended to represent the same or analogous features or elements of the present invention.

DETAILED DESCRIPTION OF PREFERRED EMBODIMENTS

Reference will now be made in detail to various embodiments of the invention, one or more examples of which are illustrated in the accompanying Figures. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used with another embodiment to yield a still further embodiment. Thus, it is intended that the present invention cover such modifications and variations as come within the scope of the appended claims and their equivalents.

In general, the present invention is directed to micro- and nano-sized electromechanical systems including micro- or nano-sized elements that can be electrostatically driven to resonance. More specifically, utilizing the disclosed devices and methods, direct electronic detection of the resonant frequency, changes of the resonant frequency, and associated phase signal of a micro- or nano-sized element such as a cantilever or double-clamped beam is possible. According to the present invention, resonance of an element can be directly detected through analyses of the electronic signal induced in the element at resonant vibration. For instance, one or both of the amplitude and phase of an electronic signal generated in the element at resonance can be directly detected and analyzed. Beneficially, changes in the resonant frequency of an element can be directly determined at ambient temperatures and pressures according to one embodiment of the disclosed invention.

The presently disclosed processes and systems can facilitate the formation of economical, portable NEMS and MEMS devices suitable for use in practical, real-world applications. The disclosed methods can be utilized with other devices as well, for instance, the disclosed methods can be utilized in development of high quality electronic filters as well as other high quality (high Q factor) electronic devices.

The devices of the present invention can include one or more micro-sized or nano-sized elements. For example, the devices can utilize one or more micro-sized beams as have been utilized as micro-sized cantilevers in previously known devices that utilize optical or piezoresistor resonance detection schemes. In general, micro-sized beams can be classified as those having micrometer dimensions, e.g., greater than about 1 µm in width and/or thickness. For example, micro-cantilevers of the present invention can have a length dimension less than about 500 µm, for instance between about 90 µm and about 350 µm and a width dimension less than about 50 µm, for instance between about 10 µm and about 50 µm, for instance about 35 µm wide. Nano-sized elements of the present invention generally include those elements having width and/or thickness dimensions less than the micro-sized devices (e.g., less than about 1 µm). For instance, in one embodiment, nano-sized elements of the invention can have a width and/or thickness dimension less than about 500 nm. Nano-sized elements can, however, have a length in the micrometer range. For instance, one exemplary nano-cantilever of the invention can have a generally circular cross-section of between about 1 nm and about 200 nm in diameter, and a length in the micrometer range, for instance greater than about 5 µm.

In general, the elements of the devices can have any geometric shape and can have an aspect ratio (L/D) greater than about two. As such, throughout much of the following discussion, the elements of the present invention are synonymously referred to as beams. Moreover, though much of the following discussion is directed to embodiments in which the elements or beams of the invention are provided in a device as a cantilever, i.e., clamped at a first end and free to vibrate at a second end, the presently disclosed methods and devices are equally applicable to an element provided in other orientations. For example, the invention is also directed to devices in which the disclosed element is clamped at both ends, i.e., a double-clamped beam. In particular, the presently disclosed invention encompasses any micro- or nano-sized element that can be electrostatically driven into resonance.

The elements of the disclosed devices can generally be formed of any material including a suitable conductive or semi-conductive material at least at the surface of the element. For instance, in one embodiment, an element can be formed of a non-conductive base substrate that has been coated with a conductive outer layer. Fabrication materials and techniques for forming many structures suitable for use in the presently disclosed devices are generally known to those of ordinary skill in the art. For example, materials encompassed by the invention include metallic nanowires, gallium arsenide/aluminum arsenide structures, nanocrystalline diamond films, and materials based upon silicon including, but not limited to, silicon on insulator structures, silicon carbide on silicon structures, aluminum nitride on silicon structures, and amorphous silicon nitride structures.

In one embodiment, the elements of the disclosed devices can be nanostructures, and in one particular embodiment, carbon-based nanostructures. For example, carbon-based nano-cantilevers of the disclosed devices can be formed from nanotubes, including single-walled nanotubes (SWNT) and multi-walled nanotubes (MWNT), nanobelts, nanorods, nanowires, nanocoils, and the like. In addition, the elements can be formed of more than one nanostructure in combination, for example, a bundle of nanotubes, or a stack of nanobelts, or even combinations of two or more structures of different shapes. Nanostructures of the invention are not limited to carbon-based nanostructures, however, and nanostructures formed of other material can be utilized. For example, nanostructures etched from silicon or including any other suitable conductive or semi-conductive material at the surface can be utilized.

Carbon nanostructures are known to exhibit exceptional physical strength, elasticity, adsorption capability, and high specific surface area. In addition, mechanical characteristics of individual carbon nanostructures have been found to be sensitive to physical characteristics of the structures that can be affected via formation materials and methods. For example, the bending modulus of individual nanostructures has been found to be sensitive to the density of wall defects formed in the structure. As such, the elements of the present invention can, in one embodiment, be specifically designed with particular, predetermined mechanical characteristics, such as a particular bending modulus, for instance, for utilization in a particular environment or for detection of a particular species or analyte.

The ability of carbon nanostructures to quickly adsorb materials is of benefit to the disclosed devices in certain sensing applications. For instance, upon adsorption of a sample material onto an element, e.g., a carbon-based nano-cantilever, the inherent physical properties of the element can be affected. In particular, the elastic properties and the natural resonant frequency of the element can vary depending upon exactly what substances have been adsorbed. Thus, a shift in resonant frequency can be observed upon adsorption of a substance. Moreover, this shift can vary depending on what material has been adsorbed. Beneficially, as many materials that can form the disclosed elements are naturally highly adsorbent, certain embodiments of the present invention may not require pre-functionalization of the element, and as such, the formation processes for such embodiments can be relatively simple and inexpensive.

In general, the elements of the disclosed devices can be formed according to any known formation method and of any suitable material. For example, carbon-based nano-cantilevers of the invention can be formed via physical evaporation methods such as vapor-liquid-solid (VLS) processes, chemical vapor deposition (CVD) methods, catalyst assisted processes, processes involving electric arc gas discharge, or pulsed laser ablation techniques, as are generally known to those of ordinary skill in the art.

In addition, the physical characteristics such as the bending modulus of the beams can be altered through selection of particular formation methods, functionalization of the base materials, and/or addition of dopants to the materials. As such, elements of the invention can be engineered so as to exhibit particular physical characteristics for use, for example, in a particular environment or for detection of one or more particular analytes from a sample.

In certain embodiments of the present invention, the disclosed devices can be made more sensitive by degassing the material forming the element. In this particular embodiment, the devices can respond to the presence of species, such as in a gaseous or vaporous sample, in concentration levels as little as about 100 ppb. In addition, when the material is degassed prior to use, the devices can have measurable response to an increased number of materials. For example, when utilizing degassed carbon-based nanostructures, systems of the invention can indicate a measurable variation in resonant frequency upon exposure to polar as well as non-polar materials.

Figure 9:
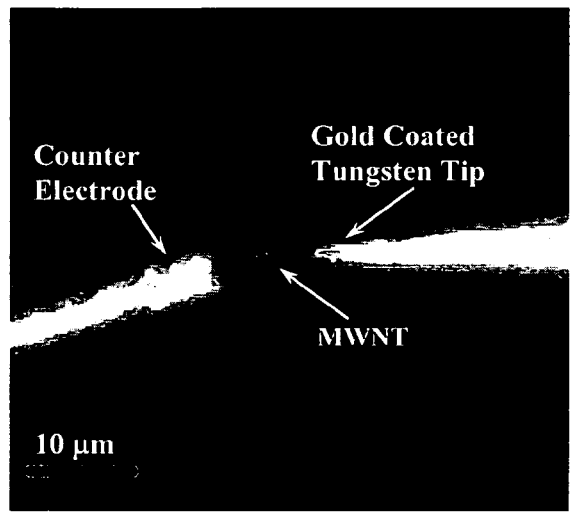
FIG. 9 is a dark field image of a tip to tip configuration of a nano-cantilever according to one embodiment of the present invention.

One embodiment of a cantilever-based device of the present invention is schematically illustrated in FIG. 1. As can be seen in the Figure, the system can include a cantilever assembly 10 that can include a micro- or nano-sized cantilever 8 in proximity to a counter electrode 6 in a tip-to-tip arrangement. FIG. 9 is a dark field image of one such embodiment of a cantilever assembly in which the cantilever 8 and the counter electrode 6 are in tip-to-tip association with one another. The cantilever in this particular embodiment is a single MWNT. FIGS. 3A and 3B illustrates another possible arrangement of the cantilever assembly 10 of the present systems in which the cantilever 8 and the counter electrode 6 are in a parallel arrangement.

Referring again to FIG. 1, the system can also include a signal generator 12 to generate an ac voltage that can be applied to the counter electrode 6 at varying frequencies. In general, a dc offset can also be supplied, as at 14, and also applied to the counter electrode 6. The dc offset can balance the difference between surface work functions of the counter electrode and the cantilever, respectively. The dc offset can also be utilized to modify the amplitude and frequency of the resonance, providing the capability of tuning the circuit, which can be useful in a number of electronic devices and applications.

The counter electrode 6 can be in close enough proximity to the element, e.g., the cantilever 8, so as to induce a charge on the element while remaining in a non-contact mode. The preferred gap distance between the counter electrode 6 and the cantilever 8 can vary, and can depend, for instance, upon the nature of the atmosphere surrounding the system and on the geometric relationship between the cantilever and the counter electrode. In general, however, the intervening distance between the cantilever 8 and the counter electrode 6 can be at least enough so as to ensure no contact between the counter electrode and the cantilever at resonance, while ensuring the capability of establishing a capacitance driven electrostatic force on the cantilever.

The voltage applied to the counter electrode can induce an electrostatic force on the cantilever, which, at the appropriate parameters, can force the cantilever into resonance. In one particular embodiment, a modulated voltage can be applied, so as to induce a modulated electrostatic force on the cantilever. In the tip to tip configuration, a tunneling gap could be created between the cantilever and the counter electrode and the tunneling current used as the signal.

According to the present invention, the unique characteristics of a system at resonance have been recognized and utilized to provide a method for direct electronic detection of a signal generated by a micro- or nano-sized element at resonance. More specifically, the presently disclosed methods and systems recognize and utilize the fact that at resonance, the force between the counter electrode 6 and the cantilever 8, and thus the charge induced in the cantilever, not only includes a term that oscillates at the resonant frequency, $\omega_o$, but also includes terms that oscillate at the higher harmonics of the resonant frequency, i.e., $2\omega_o$, $3\omega_o$, etc.

While not wishing to be bound by any particular theory, it is believed that when a voltage $V(t)=V_{dc}+W+V_{ac}\cos(\omega t)$ is placed on the counter electrode (where $V_{ac}\cos(\omega t)$ and $V_{dc}$ are the applied ac and dc voltages, and W is the difference between the work potentials of the cantilever and counter electrode) and when $\omega$ approaches $\omega_0$ (the resonant frequency of the cantilever) the harmonic terms of the resonating cantilever can be detected. According to the theory, let C(t) be the capacitance between the cantilever and the counter electrode. The electrostatic energy of the system is then $\frac{1}{2}CV^2$, and the force on the cantilever is $$F = -1/2 \frac{dCV^2}{dx}$$
$$= -1/2 V^2 \frac{dC}{dx}.$$

If the vibration amplitude x(t) of the cantilever is small compared to the distance $x_0$ between the cantilever and the counter electrode, then $$C(t) \approx C_0 + \frac{dC}{dx}\bigg|_{x=0} x(t),$$

where $C_0$ and $$\frac{dC}{dx}\bigg|_{x=0} = -C'_0$$

are constants for a given experimental set up. Thus for small deflections, the Coulomb force on the cantilever is $$F_c = 1/2 C'_0 (V_{dc} + W + V_{ac}\cos(\omega t))^2 \quad \text{S(1)}$$

$$= 1/2 C'_0 \left\{ \begin{array}{l} (V_{dc}+W)^2 + 2(V_{dc}+W) \\ V_{ac}\cos(\omega t) + \frac{1}{2}V_{ac}^2[1+\cos(2\omega t)] \end{array} \right\}$$

(Note that $C'_0$ is a function of the geometry of the system.) If the vibration amplitude is not small compared with the separation of the counter electrode and the cantilever, or if the geometry of the capacitance is complex, terms of higher order in x(t) may have to be considered. When $\omega$ is close to a normal mode frequency $\omega_0$ of the free cantilever, and the damping is small, the steady state solution for x(t) is $$x(t) = \frac{QC'_0(V_{dc}+W)V_{ac}\cos(\omega t - \phi_1)}{k'\sqrt{Q^2\left[1-\left(\frac{\omega}{\omega'_0}\right)^2\right]^2 + \frac{\omega^2\omega_0^2}{\omega'^4_0}}}, \quad \text{S(2)}$$

$$\tan\phi_1 = \frac{\omega_0\omega}{Q(\omega'^2_0 - \omega^2)}$$

where $$\omega'^2_0 = \frac{k'}{m}, k' = k - \frac{dF_c}{dx},$$

m is the inertial term of the vibrational mode, and Q the quality factor of the mode in the environment of the experiment. The electrostatic correction term $$\frac{dF_c}{dx}$$

is usually small, as discussed below, so that $\omega_o'$ is not very different from $\omega_o$. Since F also has a term that oscillates at $2\omega$, when $2\omega$ is close to $\omega_o$ a similar analysis gives:

$$x(t) = \frac{QC'_0 V_{ac}^2 \cos(2\omega t - \phi_2)}{4k'\sqrt{Q^2\left[1-\left(\frac{2\omega}{\omega'_0}\right)^2\right]^2 + \frac{4\omega^2\omega_0^2}{\omega'^4_0}}}, \quad \text{S(3)}$$

$$\tan\phi_2 = \frac{2\omega_0\omega}{Q(\omega'^2_0 - 4\omega^2)}$$

Since q(t)=C(t)V(t), to first order in x(t), we obtain for the time dependent part of q:

$$q(t) = \left[C_0 - \frac{QC_0'^2(V_{dc}+W)V_{ac}\cos(\omega t - \phi_1)}{k'\sqrt{Q^2\left[1-\left(\frac{\omega}{\omega'_0}\right)^2\right]^2 + \frac{\omega^2\omega_0^2}{\omega'^4_0}}}\right] \omega \text{ near } \omega_0 \quad \text{(S4)}$$

$$[V_{ac}\cos(\omega t)]$$
$$= [C_0 V_{ac}\cos(\omega t)] -$$
$$= \left[\frac{QC_0'^2(V_{dc}+W)V_{ac}}{2k'\sqrt{Q^2\left[1-\left(\frac{\omega}{\omega'_0}\right)^2\right]^2 + \frac{\omega^2\omega_0^2}{\omega'^4_0}}}\right]$$
$$[\cos(2\omega t + \phi_1) + \cos\phi_1]$$

and $$q(t) = \left[C_0 - \frac{QC'_0 V_{ac}^2\cos(2\omega t - \phi_2)}{4k'\sqrt{Q^2\left[1-\left(\frac{2\omega}{\omega'_0}\right)^2\right]^2 + \frac{4\omega^2\omega_0^2}{\omega'^4_0}}}\right] \omega \text{ near } \frac{\omega_0}{2} \quad \text{(S5)}$$

$$[V_{ac}\cos(\omega t)]$$
$$= [C_0 V_{ac}\cos(\omega t)] -$$
$$\left[\frac{QC'_0 V_{ac}^2}{8k'\sqrt{Q^2\left[1-\left(\frac{2\omega}{\omega'_0}\right)^2\right]^2 + \frac{4\omega^2\omega_0^2}{\omega'^4_0}}}\right]$$
$$[\cos(3\omega t - \phi_2) + \cos(\omega t - \phi_2)]$$

Thus, for ω near $\omega_o$, the denominator of the second terms in eqns. S3 and S4 becomes small, and q(t) oscillates with large amplitude at 2ω, the second harmonic of the applied angular frequency, ω. For ω near $\omega_o/2$, q(t) oscillates with large amplitude at 3ω, the third harmonic of the applied angular frequency, as well as at the first harmonic.

As an illustration, if the resonant frequency of a mode is $\omega_0 \approx 20$ kHz, q(t) will have maxima for 2ω near 20 kHz (or ω near 10 kHz) and for ω near 20 kHz (cf. eqn. S1). When ω is near 10 kHz, q(t) will have a large Fourier component near 30 kHz (cf. eqn. S5). When ω is near 20 kHz, q(t) will have a large Fourier component near 40 kHz (cf. eqn. S4). In both cases, the fundamental of the applied frequency is present without any vibration x(t) of the cantilever, due to parasitic capacitance as well as the first term $C_0 V_{ac} \cos(\omega t)$ in eqns. S4 and S5, so that measuring the charge on the cantilever at the fundamental frequency will not show a large effect at the normal mode frequency.

Thus even in the case when the vibrations of the cantilever are small enough to enable a linear theory, the second and third harmonics should be large. When the vibrations are not small with respect to the distance between the cantilever and the counter electrode, nonlinearities and parametric effects are expected that would increase further the importance of the higher harmonics in q(t).

The difference between k and k' (and thus between $\omega_o$ and $\omega_o'$) can be tuned by the applied ac and dc voltages. This effect is small, but because of the large Q factors it is easily observable, even in nanotubes. The electrical forces perturb k to k' by an amount $$\frac{dF_c}{dx}.$$

Now, $$\frac{dF_C}{dx} = \frac{d\left\{\begin{array}{l} 1/2(C_0'(V_{dc}+W))^2 + 2(V_{dc}+W) \\ V_{ac}\cos(\omega t) + \frac{1}{2}V_{ac}^2[1+\cos(2\omega t)] \end{array}\right\}}{dx} \quad S(6)$$

$$= -1/2\left[\frac{d^2C}{dx^2}\right]_{x=0}\left\{\begin{array}{l}(V_{dc}+W)^2 + 2(V_{dc}+W) \\ V_{ac}\cos(\omega t) + \frac{1}{2}V_{ac}^2[1+\cos(2\omega t)]\end{array}\right\}$$

The time dependent terms will average out (but contribute to the higher harmonics), so that the resulting change in the observed frequency is proportional to the second derivative of the capacitance of the system with respect to x, and to $[(V_{dc}+W)^2 + \frac{1}{2}V_{ac}^2]$. It has been found experimentally (see the following Example section) that there is a decrease in the resonant frequency as $V_{ac}$ is varied (cf. FIGS. 6 and 8), in agreement with this treatment.

In the tip-to-tip configuration, the charges accumulated at the tip of a cantilever and on the counter electrode can be assumed to be quasi point charges, Q, which can be expressed as:

$$Q = \alpha[(W_{AU} - W_{MWNT}) + e(V_{dc} + V_{ac}\cos 2\pi f_E t)]$$

where α is a geometrical factor related to the counter electrode geometry and the charges are separated by a distance R. The Coulomb force, $F_e$, between the charges on the counter-electrode tip and cantilever is given by $$F_e = \frac{1}{4\pi\varepsilon_o\varepsilon_r R^2}Q^2$$

$$= \frac{\alpha^2}{4\pi\varepsilon_o\varepsilon_r R^2}[A_{DC} + A_{f_E}\cos 2\pi f_E t + A_{2f_E}\cos 4\pi f_E t]$$

where $$A_{DC} = [(W_{Au} - W_{MWNT}) + eV_{dc}]^2 + e^2\frac{V_{ac}^2}{2};$$

$$A_{f_E} = 2eV_{ac}[(W_{Au} - W_{MWNT}) + eV_{dc}]$$

and $A_{2f_E} = e^2 V_{ac}^2/2$. For small oscillations, the excitation y of each normal mode can be expressed as a forced oscillator with damping $$b\frac{\partial y}{\partial t}$$

$$m_e\frac{\partial^2 y}{\partial t^2} + b\frac{\partial y}{\partial t} + k_e y = F_e,$$

where the $m_e$, $k_e$ and $F_e$ are the mass, elastic constant and force for an equivalent oscillator driven at frequency $f_E$. When $f_i$ is near $f_E$, the steady state solution for the above equation can be written as:

$$y = \frac{\alpha^2}{4\pi\varepsilon_o\varepsilon_r R^2}\frac{A_{f_E}}{2\pi\sqrt{m_e^2(f_E^2 - f_i^2)^2 + b^2 f_E^2}}\sin(2\pi f_E t - \delta),$$

where the phase shift δ for the mode with frequency $f_i$ is given by:

$$\delta = \cos^{-1}\left(\frac{bf_E}{\sqrt{m_e^2(f_E^2 - f_i^2)^2 + b^2 f_E^2}}\right)$$

The resonant frequency of the element can be obtained by finding the excitation frequency that matches the natural mode frequency. Note that similar expressions can be obtained for a steady state solution when $f_i$ is near $2 f_E$.

There can also be a charge oscillating at frequency ω induced on the assembly by parasitic capacitances that exist between components of the circuitry, leading to the presence of electronic noise in the generated signal. However, as this is not at resonance, the noise signal will not include any harmonic terms, and thus can be separated from the signal generated due to the resonance of the element through utilization of the harmonic components of the resonant signal.

According to the present invention, the signal generated from the charge induced at resonance, and in particular, the angular frequency, amplitude, and phase of the signal generated, can be detected and analyzed through utilization of the harmonic components of the signal. These components of the signal can be separated from the fundamental mode of the signal and noise due to parasitic capacitance through use of a signal processor such as a lock-in amplifier. For example, and referring again to FIG. 1, down line of the cantilever assembly 10, the device can include an optional low noise amplifier 13 to provide signal enhancement. For instance, a charge sensitive preamplifier, such as the A250 charge-sensitive preamplifier available from the Amptek Corporation of Bedford, Mass., can be placed in the line following the cantilever assembly 10.

Down line from the optional low noise amplifier 13 a signal processor 16 can be located. For example, a lock-in amplifier can be utilized as the signal processor 16. In this particular embodiment, the drive signal provided from the signal generator 12 can be fed to the lock-in amplifier 16, as shown, but the reference signal of the lock-in, rather than being set to the frequency of the generated signal, $\omega$, can be set to a higher harmonic of the generated signal, i.e., $2\omega$, $3\omega$, etc. As the signal output from the lock-in can be set so that it represents essentially only frequencies very close to a higher harmonic in the input signal from the amplifier when near resonance, i.e., when $\omega=\omega_o$, and the amplitude of this higher harmonic signal can be greater than that of the signal due to noise of the system, the output from the lock-in amplifier can be used to clearly and unambiguously determine the resonant frequency of the cantilever assembly. When the voltage applied to the counter electrode induces the natural resonant frequency of the cantilever, the signal generated at the cantilever can demonstrate that resonance through, for example, greatly increased signal amplitude and phase shift, either or both of which can then be observed at the lock-in amplifier during signal examination for the harmonics of the applied charge.

If desired, the signal sent to the signal processor 16 can be modified from that generated at the signal generator 12. For example, in one embodiment, the signal from the signal generator 12 can be sent into a frequency modifier that can double or triple the frequency of the signal prior to sending the signal into a lock-in amplifier as a reference signal. According to this particular embodiment, the signal provided to the lock-in amplifier on this line can have a frequency identical to a multiple of the frequency of the signal generator, and thus the lock-in will be sensitive to that multiple of the signal applied to the counter electrode. According to this embodiment, a lock-in could be used without the necessity of an internal circuit for measuring the higher harmonics of the resonant frequency.

The methods and systems of the present invention are not limited to utilization of a lock-in amplifier for processing the signal from the assembly 10 and detecting the resonance of the cantilever. It should be understood that any electronic detection system as is known in the art can be utilized according to the presently disclosed methods to detect the higher harmonics that will exist in the signal induced at resonance. For example, in another embodiment, a phase detector can be utilized to detect differences in phase between the signal induced at the cantilever assembly and the signal supplied from the signal generator. Phase detectors may be employed using a circuit that extracts the phase out of the signal induced at the cantilever in real time, similar to the manner in which the frequency of the signal is reconstructed from lock-in outputs. A suitable phase locked loop (PLL) circuit may be used for this purpose. The combination of a PLL and a voltage controlled oscillator may be used to provide feedback that sharpens the resonance and provides a signal proportional to $\omega_0$.

Beneficially, due to the improved resonance sensing capability, the electrostatic capacitance at the junction of the resonating element with the counter electrode need not be maximized through minimization of the size of the gap distance, as has been the case in previously capacitance-based NEMS and MEMS. As such, the gap distance between the counter electrode and the element can be much larger in the disclosed devices than thought possible in NEMS and MEMS of the past, and resonance can still be easily and accurately determined according to the disclosed method. For instance, in one embodiment, resonant frequency can be determined for nano-sized cantilevers in a system including the cantilever and the counter electrode in a parallel configuration and at gap distance greater than about 1 $\mu$m, or greater yet, for example, about 2 $\mu$m in some embodiments. When considering systems of the present invention including nano-cantilevers in a tip-to-tip arrangement with the counter electrode, resonance can be induced and detected at gap distances of up to about 200 nm. Systems of the invention incorporating micro-cantilevers can have resonant frequency discerned at gap distances previously considered too large for detection. For instance, resonance can be induced and unambiguously detected in systems in a parallel configuration with a gap distance of greater than about 10 $\mu$m according to the presently disclosed methods. The gap distance can be even larger in other embodiments, for instance greater than about 20 $\mu$m.

In addition to determining the change in the resonant frequency, sensors of the invention can also detect and analyze the change in the Quality factor (Q-factor) of the element. While not a requirement of the present invention, analysis of the Q-factor can serve as an additional variable to monitor a change in resonant frequency of the element. Particularly high Q-values are possible when utilizing the disclosed devices in a vacuum. For instance in some embodiments of the present invention, Q-values greater than about 10,000 are possible. As is generally known, the Q-value can generally be considered to be equal to the energy of the oscillating element divided by the energy loss to dissipative forces in one cycle. In one embodiment, the disclosed devices can be utilized as chemical sensors.

In one embodiment of the present invention, an element as herein described can be contacted with a gaseous, vaporous, or liquid stream containing a species. According to this embodiment, the device can define a fluid flow field such as a channel or porous web or membrane for flowing a liquid species to the element or a contained line or chamber to encourage the flow of a gaseous or vaporous species to the element. In any case, the fluid flow field can provide direction to a fluid flow such that the fluid that carries the species, be it liquid, gas, or vapor, can interact with the element. For instance, the fluid flow field can contact the element such that the species contained in the fluid can interact with the element through direct contact.

Upon interaction between the species and the element, for example, upon adsorption of the species to a surface of the element, a change in the resonant frequency of the element can occur that can then be detected as herein described. Moreover, this shift can vary in characteristic depending upon the species. Thus, the shift in resonant frequency of the element upon interaction of the species with the element can be utilized to identify the species.

In some embodiments, characteristics of the shift in the resonant frequency can also be proportional to the concentration of the detected species. As such, in certain embodiments, the disclosed sensors can also be utilized to quantify the cause of the shift in charge characteristics, e.g., the concentration of a detected species. For instance, the disclosed systems can be advantageously utilized in recognizing and determining extremely small masses, i.e., as a micro- or nano-balance.

Optionally, sensors of the present invention can be designed so as to bind a particular species of interest. For instance, a semiconductive or conductive cantilever as herein described can be pre-treated so as to preferentially bind an analyte of interest, and the sensor can then be utilized to detect that specific analyte. For example polyclonal or monoclonal antibodies as are generally known in the art could function as a binding agent for an analyte specific to that antibody, such as *Aspergillus niger* spore analytes, for instance. Any suitable method can be utilized to attach the binding agent to a cantilever. For instance, pentaerythritol tetranitrate and hexahydro-1,3,5-triazine, both which can bind to a silicon microcantilever with its gold surface modified with a self-assembled monolayer of 4-mercaptobenzoic acid, can be utilized to attach the binding agent to a cantilever. In one particular embodiment the disclosed systems and methods can be utilized in biosensing, enabling the detection of extremely small amounts of biological species.

In one embodiment, the present invention can be used to detect species at very low concentrations. For instance, as the disclosed devices can operate in the microwave regime, the presence of species in concentrations as low as parts per billion can lead to a discernable shift in the resonant frequency of the device.

The devices and electronic detection regimes of the present invention can be utilized in many applications, in addition to species sensing applications such as those described above. For instance, the disclosed methods and devices can be utilized in applications directed to detecting changes in the surrounding atmosphere. For example, the devices can be used to detect changes in surrounding pressure, such as those due to atmospheric change or atmospheric acceleration, changes in surrounding magnetic forces, or changes in temperature. Moreover, and similar to the species sensing applications described above, characteristics of the shift in the resonant frequency can also be proportional to the strength of the environmental change causing the shift. Accordingly the sensors can be utilized to quantify the environmental changes leading to the shift in resonant frequency of the element.

In one embodiment, the devices and regimes disclosed herein can be utilized to detect an alteration in a species due to a particular environmental condition, and thereby can be utilized to detect the environmental condition. For example, a species that will undergo characteristic change in the presence of an environmental condition can be isolated with a sensor as described herein. Following exposure to the environmental condition, the characteristic change in the species can be reflected in a change in the resonant frequency of the device. Hence the existence of the underlying cause of the change, i.e., the environmental condition, can be established. For instance, upon exposure to radiation, many known species can undergo a characteristic change that can lead to a discernable shift in the resonant frequency of a sensor near the species.

Figure 15:
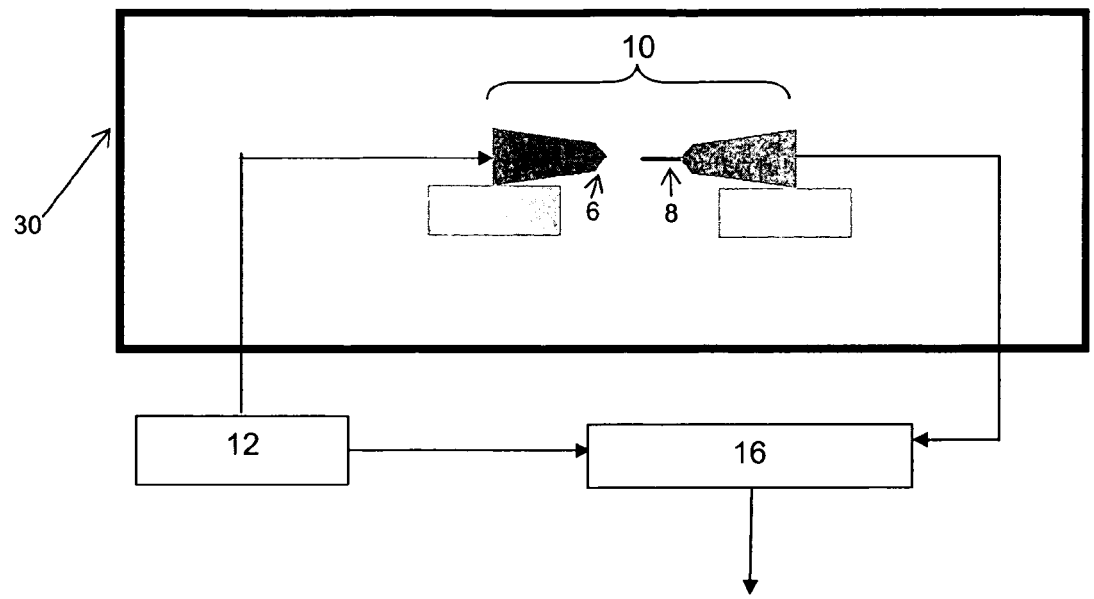
FIG. 15 schematically illustrates a sensor according to one embodiment of the present invention.

One specific embodiment of such a system is schematically illustrated in FIG. 15. As can be seen, a cantilever assembly 10 can be isolated in a chamber 30. For instance, the chamber 30 can be a vacuum chamber partially filled with a species, such as argon. In the presence of radiation, the argon atoms can be ionized, and be electrostatically attracted towards the cantilever 8. This can result in a shift in the resonant frequency of the cantilever 8 that can be monitored and detected as described above.

The systems of the present invention can also be beneficially incorporated into other devices as well. For example, the capability of direct electronic determination of the resonance of a micro- or nano-sized cantilever can be beneficially incorporated into any device that can employ cantilever-based NEMS or MEMS. The disclosed methods can beneficially be utilized in formation of switching devices, electronic sending/receiving devices, or any NEMS or MEMS device based upon the use of dynamic capacitance or electrostatic actuation and detection.

Figure 16:
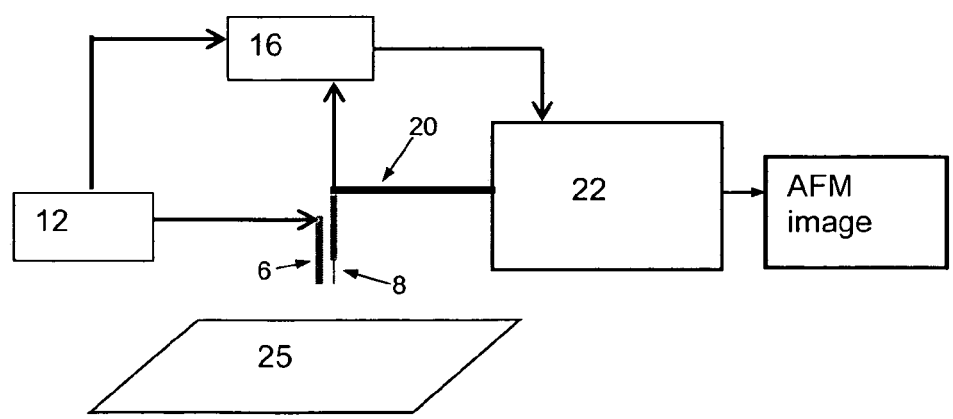
FIG. 16 is a schematic illustration of one embodiment of an AFM system utilizing methods and devices of the present invention.

In one embodiment, the methods and devices disclosed herein can be utilized in sensing/imaging techniques such as atomic force microscopy (AFM). One embodiment of an AFM according to the present invention is illustrated in FIG. 16. As can be seen with reference to the Figure, a cantilever 8 can be electrostatically driven to oscillate at its resonant frequency due to the electrostatic force of a voltage applied to counter electrode 6 via a signal from signal generator 12. The resonance of the cantilever 8 can be determined and monitored as described above through utilization of a suitable signal processor 16, such as a lock-in amplifier. In addition, the cantilever 8 can be in mechanical communication with an AFM arm 20 that is capable of motion and controlled with AFM system 22 as is generally known in the art. During use, the location and motion of AFM arm 20 can be controlled in response to signal information obtained from the signal processor 16, as shown. As the cantilever approaches a sample held on stage 25, atomic forces between the cantilever 8 and the sample can cause a changes in the resonant frequency of the cantilever. A feedback loop between the signal processor 16 and the AFM arm 20 can adjust the height of the cantilever 8 over the sample in order to keep the cantilever 8 at resonance. Information concerning the height of the AFM arm 20 at resonance can then be collected to create data points by the AFM system 22. As data points are taken and recorded as the cantilever 8 scans the sample, a topological image of the sample can be developed according to standard AFM imaging methods as are generally known in the art. The AFM system can optionally work in non-contact or tapping mode, as desired.

The disclosed AFM systems may provide additional benefits over more traditional AFM systems when operating in tapping mode. For example, in one embodiment, as discussed above, the cantilever of the disclosed systems can include one or more carbon nanotubes. Carbon nanotubes are understood to be less fragile and more elastic than traditional AFM tips, such as those formed of silicon or silicon nitride. Accordingly, AFMs as herein described can be more resilient than previously known AFM systems, and the disclosed systems can be utilized with less down time due to probe damage and replacement as compared to more traditional systems.

In other embodiments, the disclosed devices can be utilized as switching devices, antennas, or any other device that can take advantage of the direct electronic detection of the change in amplitude and phase of the element upon a change in the resonant frequency of the element.

The present invention may be more clearly understood with reference to the Examples, below. All measurements in all Examples were performed in air under ambient conditions unless otherwise noted.

EXAMPLE 1

Figure 2:
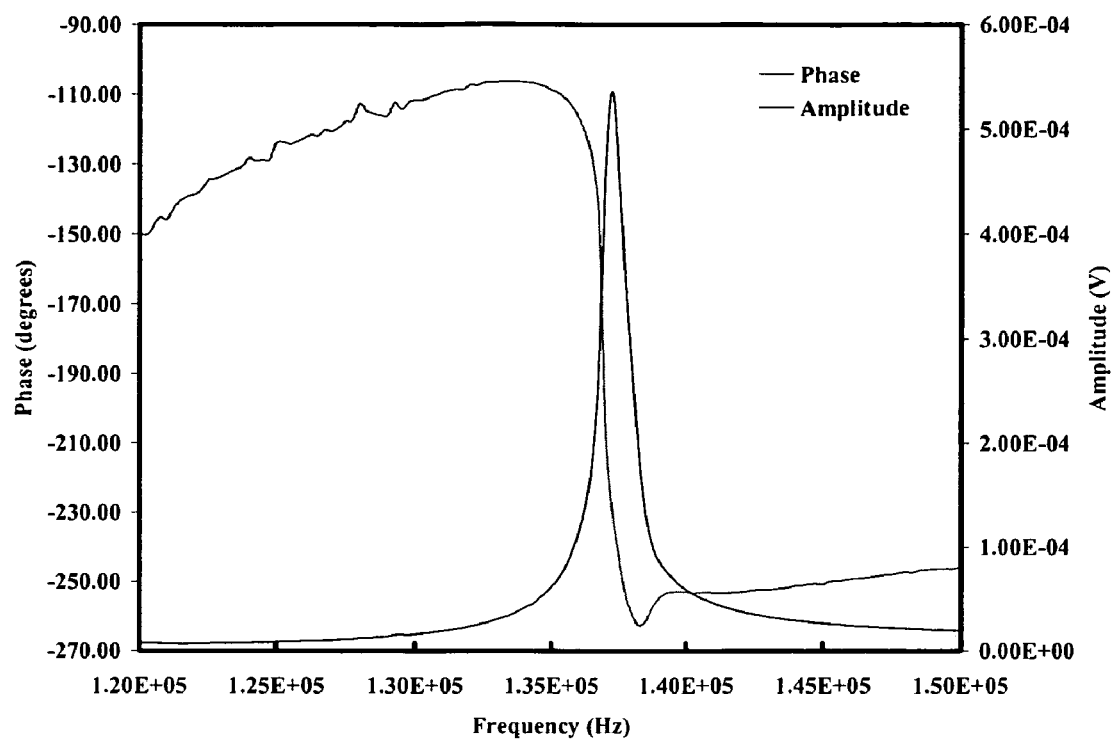
FIG. 2 graphically shows the amplitude and phase changes with regard to frequency of applied voltage for an exemplary system of the present invention including a silicon micro-cantilever.

A system similar to that illustrated in FIG. 1 was developed including a silicon micro-cantilever approximately 100 μm in length. A modulated ac charge was applied to the counter electrode at varying frequencies. The signal generated at the cantilever was analyzed at a lock-in amplifier using the second harmonic where both amplitude and phase were determined. Results are illustrated in FIG. 2. As can be seen, the resonant frequency can be clearly recognized by both an increase in frequency amplitude and phase shift.

EXAMPLE 2

Figure 3:
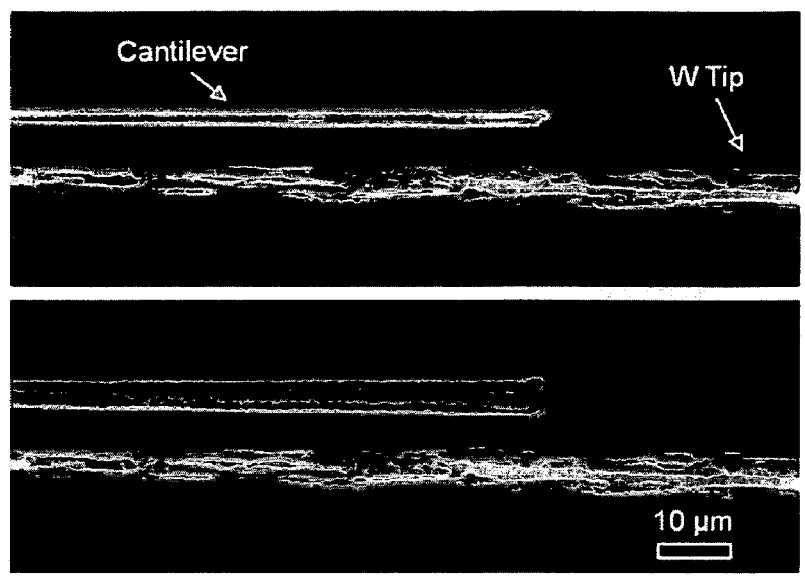
FIG. 3 is a dark field image of a parallel configuration of a micro-silicon cantilever that can be utilized according to the present invention in which the cantilever is at rest in FIG. 3A and vibrating in FIG. 3B.
Figure 4:
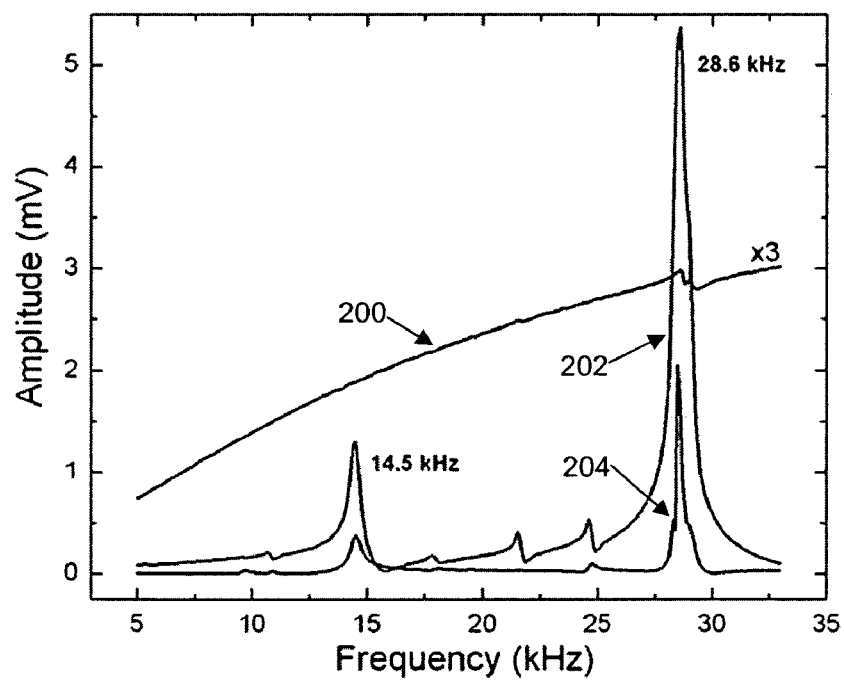
FIG. 4 graphically illustrates data obtained via one embodiment of the disclosed system.

A system such as that illustrated in FIG. 1 was constructed utilizing a commercially available tipless aluminum coated silicon cantilever with known fundamental modes (300 μm long, 35 μm wide, and 2 μm thick, available from MikroMasch) that was placed in parallel arrangement with a counter electrode, as shown in FIG. 3. In separate runs, the lock-in amplifier was set to measure the driving frequency, the second harmonic, and the third harmonic, respectively. The results are shown in FIG. 4, lines 200, 202, 204, respectively. As can be seen, when the lock-in was set to measure at the driving frequency, the weak signal generated from the movement of the cantilever at resonance was measured as a small peak riding the broad signal present, due to the parasitic capacitance. In addition, and as expected, the baseline when looking for the $1^{st}$ harmonic gradually increased with the frequency. Although there was a response at the resonant frequency, the signal to noise ratio (S/N) was very small. When this signal was instead detected at the second harmonic, the signal stemming from the parasitic capacitance was avoided, which permitted the detection of the resonant frequency ($\omega_o$) with a superior S/N. Weak peaks present between $\omega_o/2$ and $\omega_o$ were believed to be due to residual electrical pick-up, as they did not respond to changes in the applied ac or dc voltage. In addition, it was found that measuring in the $3^{rd}$ harmonic a higher Q-value was obtained than when measuring in the second. Accordingly, in some embodiments of the disclosed invention, it may be preferred to detect the resonant frequency of the cantilever via the $3^{rd}$ or even higher harmonics.

Figure 5:
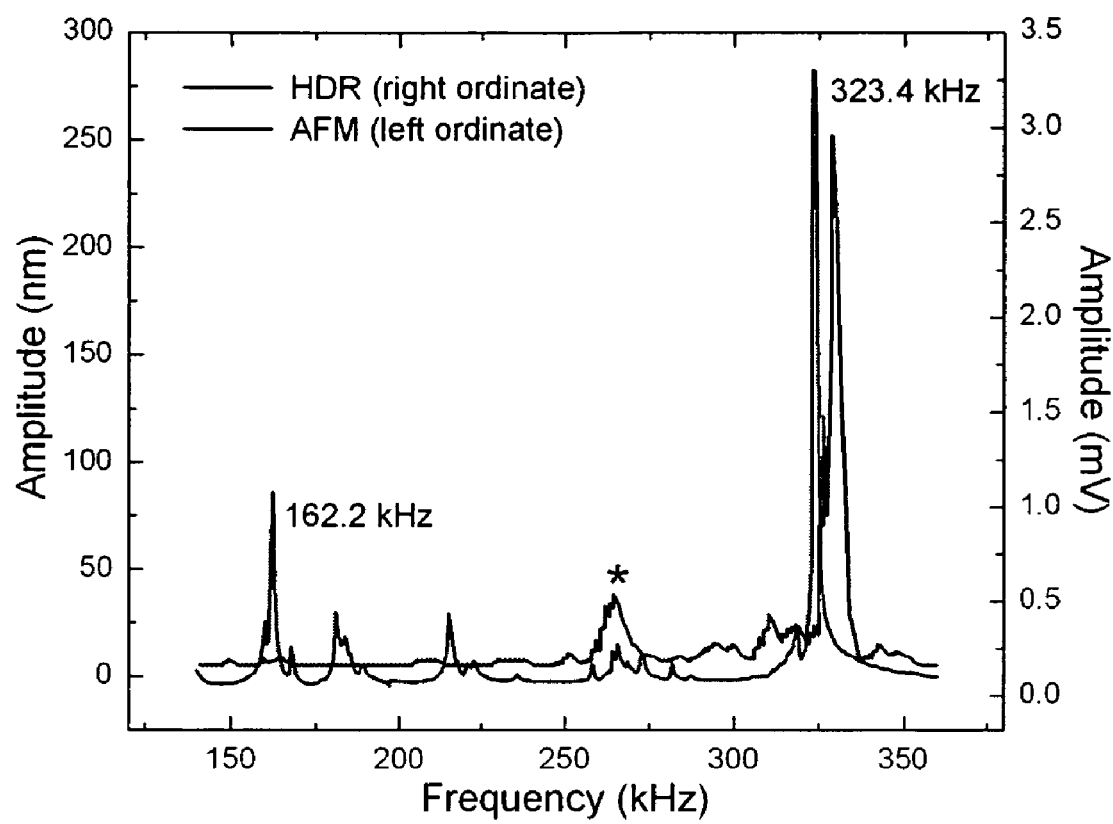
FIG. 5 compares the resonant frequency data for a silicon micro-cantilever obtained via the disclosed methods to that of the same cantilever obtained via an AFM optical technique.

FIG. 5 compares the resonant frequency obtained for a similar micro-cantilever system (cantilever dimensions were 90 μm long, 35 μm wide, and 2 μm thick) according to the disclosed methods (marked as HDR in FIG. 5, i.e., harmonic detection of resonance) to that determined from a well established optical technique which is routinely used utilizing an atomic force microscope (Veeco di-CP II) (marked as AFM in FIG. 5). The agreement between the measurements is a further indication of the efficacy of the presently disclosed techniques. The small differences in the resonant frequencies are attributed to differences in the excitation methods (piezoelectric vs. the disclosed direct methods). A quality factor Q=200 was obtained for the $2^{nd}$ harmonic detection of the fundamental mode frequency.

As can be seen, with reference to the Figures, the cantilever also vibrated when the oscillator applied a signal with frequency $\omega=\omega_o/2$. When the resonance spectrum was obtained with the AFM, the excitation was applied by a piezoelectric source, and hence no peak at $\omega_o/2$ was seen. As expected, the $1^{st}$ harmonic signal was small, and the $2^{nd}$ and $3^{rd}$ harmonic signals gave a clear indication of the resonance.

Figure 6:
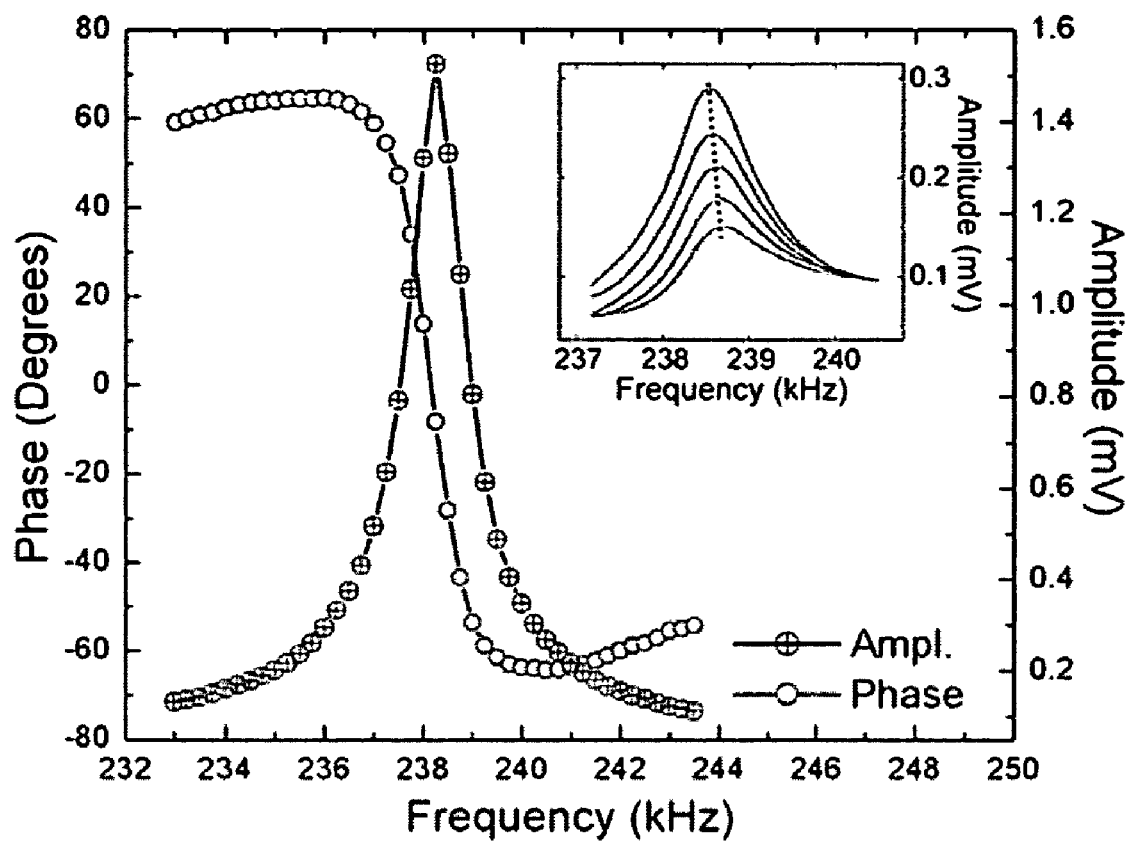
FIG. 6 illustrates the resonance spectra data for another silicon micro-cantilever.

In a separate measurement, the resonance spectrum and phase for a similar silicon micro-cantilever (110 μm long, 35 μm wide, 2 μm thick) was determined according to the present process. FIG. 6 shows that the amplitude peak is accompanied by a phase change of ~130°. It should be emphasized that according to the presently disclosed methods, the amplitude and phase can be determined simultaneously. The inset of FIG. 6 illustrates the weak dependence between the natural resonant frequency of the system and the applied ac voltage. This softening is believed to be due to a decrease in the effective spring constant of the system induced by the applied voltage.

EXAMPLE 3

Figure 7:
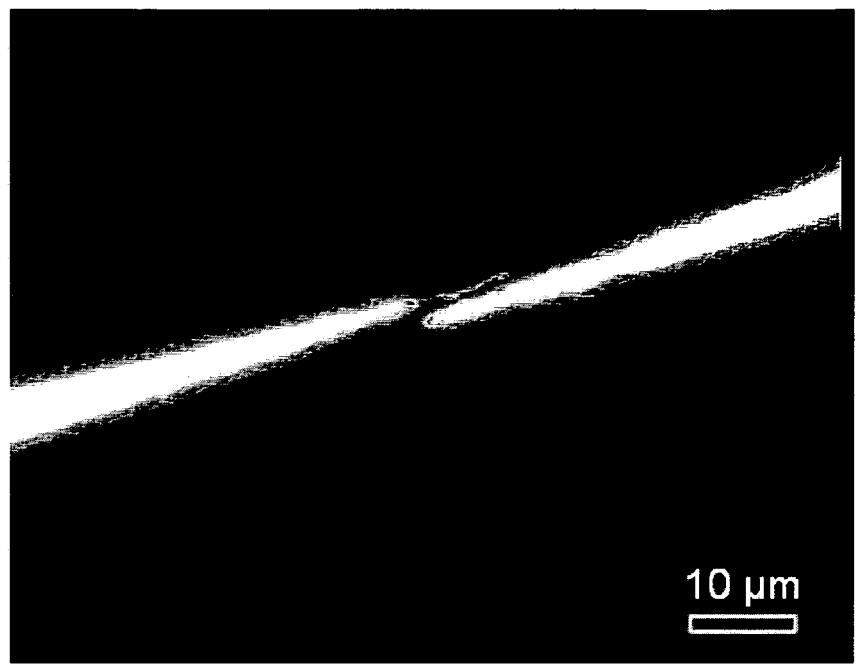
FIG. 7 is a dark field image of a MWNT nano-cantilever in parallel arrangement with a counter electrode.
Figure 8:
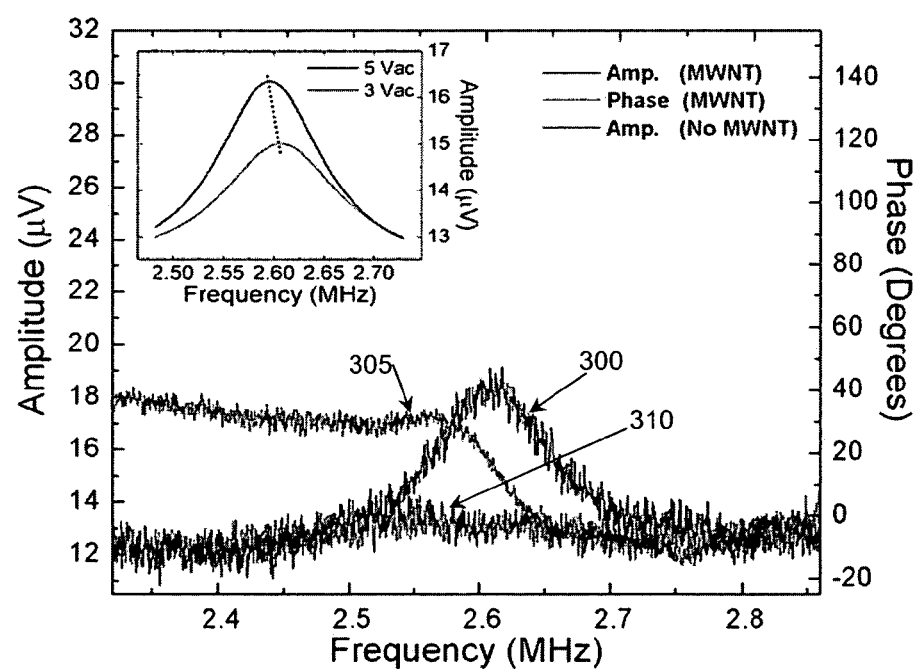
FIG. 8 displays the resonance and phase spectra for a system of the present invention including a MWNT nano-cantilever in a parallel configuration.

The resonant frequency and phase for a cantilevered MWNT was determined. A MWNT (7 μm in length, 50 nm in diameter) was mounted on a sharpened gold-coated tungsten probe and manipulated ~1 μm away from and parallel to the same gold-coated tungsten counter electrode used for Example 2. The MWNTs used in this study were grown by a chemical vapor deposition method (as further described in "Gaillard, J., Skove, M. J. & Rao, *App. Phys. Lett.* 86, 233109-233109-3 (2005)" incorporated herein by reference) utilizing a two-stage thermal CVD reactor consisting of a low-temperature (~200° C.) preheater followed by a higher-temperature furnace (~750° C.). Typical flow rates of the gases are 200 sccm (standard cubic centimeters per minute) for hydrogen and 675 sccm for Ar. In particular, the MWNTs were prepared from a catalytic decomposition of a trimethylamaine [$(CH_3)_3N$]-ferrocene (TMA/ferrocene) mixture. The MWNTs were determined to have an average diameter of ~50 nm. FIG. 7 is a dark field image of a MWNT cantilever in parallel arrangement with the counter electrode. FIG. 8 displays typical frequency (line 300) and phase (line 305) spectra obtained for the MWNTs when the system was set to ascertain the presence of the second harmonic of the drive signal in the generated signal. For comparison, the resonance spectrum was also collected in the absence of the MWNT for the same tungsten probe geometry (FIG. 8, line 310). Similar to the Si micro-cantilever of Example 2, an accompanying change in phase of about 50° was observed. This phase change value is reasonable due to the presence of noise.

EXAMPLE 4

The harmonic charge modulation detection regime of the present invention was used to measure the mechanical resonance of a single MWNT. A system similar to that shown in FIG. 1 was utilized in which the cantilever was a MWNT placed on a sharpened gold-coated tungsten probe tip. A similar probe tip was used as the counter electrode and aligned with the MWNT in a tip-to-tip arrangement as shown in FIG. 9. The alignment of the MWNT with the counter electrode was monitored using a dark field optical microscope (Nikon Epiphot 200) equipped with a digital camera (MOTICAM 1000). Both an ac voltage and a dc voltage were used to induce charge on the MWNT. The modulated charge on the MWNT was detected and amplified by a low noise charge amplifier (Amptek A250). The output signal of the LNA was detected using a lock-in amplifier set for $2^{nd}$ harmonic detection. A computerized data acquisition system collected the excitation frequency provided by the signal generator, as well as the amplitude and phase of the LNA output signal as measured by the lock-in amplifier.

Figure 10:
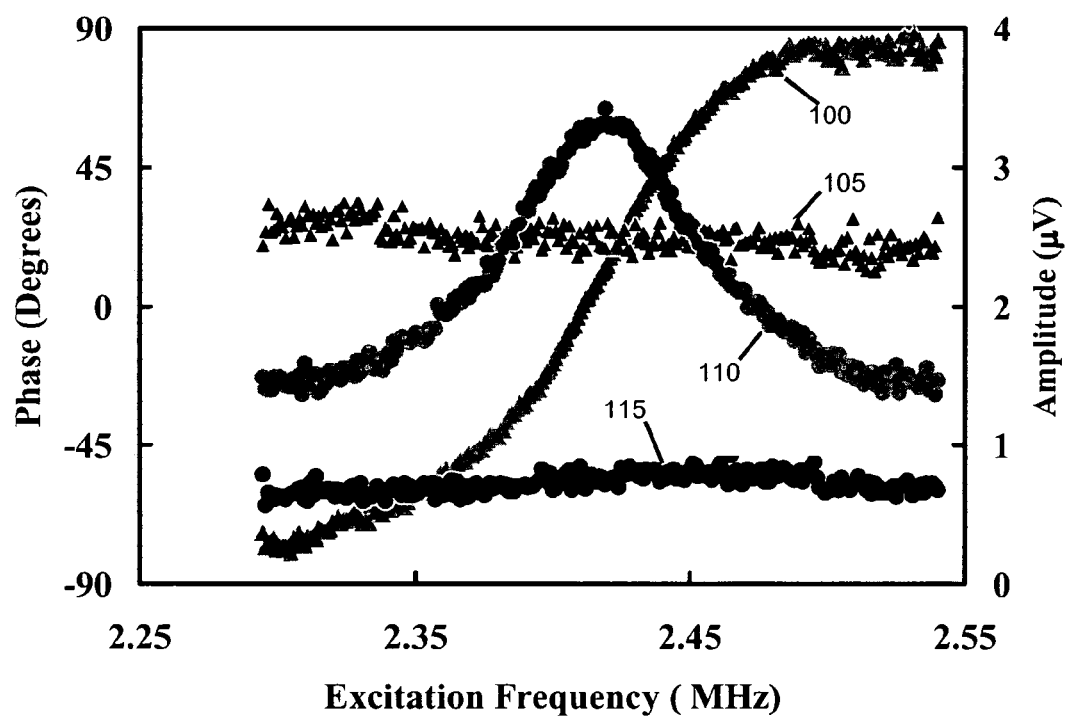
FIG. 10 shows resonance spectra data obtained for a MWNT nanocantilever according to the presently disclosed methods in the tip to tip geometry.

FIG. 10 shows the resonance spectra (phase line 100, amplitude line 110) obtained for a TMA/ferrocene CVD grown MWNT with length of 10 μm, inner diameter 17 nm, and outer diameter 57 nm. The initial gap distance ($V_{ac}=V_{dc}=0$) was estimated to be about 200 nm. As can be seen with reference to the Figure, line 100 shows an associated 160° change in phase at resonance. The maximum amplitude and phase change occurred when the exitation frequency reached 2.420 MHz, which, in this case, was the resonance at the second mode of vibration, as the lock-in was set for the $2^{nd}$ harmonic detection. For comparison, amplitude (line 115) and phase (line 105) signals were obtained for the same geometry of the electrodes in the absence of the MWNT. As can be seen, no noticeable changes in the traces for the amplitude and phase can be discerned in the frequency range between 2.250 to 2.550 MHz when the MWNT was absent.

EXAMPLE 5

The system of Example 4 was utilized, but with a gap distance between the MWNT tip and the counter electrode tip greater than that of Example 4. The second gap distance was estimated to be less than about 400 nm.

Figure 11:
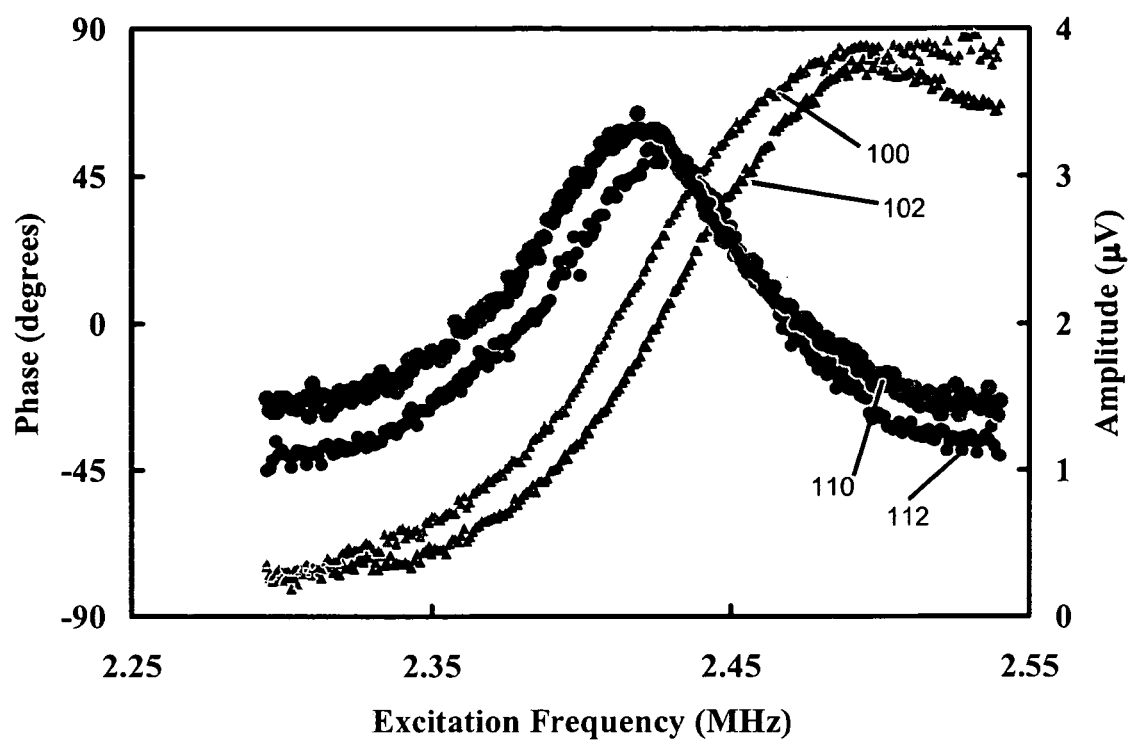
FIG. 11 compares resonance spectra for the MWNT nano-cantilever of FIG. 10 at two different gap distances in the tip to tip geometry.

FIG. 11 illustrates the resonance spectra (phase line 100, amplitude line 110) obtained for the system of Example 4 overlaid with the response of the same system at the greater gap distance (phase line 102, amplitude line 112).

The frequency at maximum amplitude was observed to increase with gap distance from 2.420 MHz to 2.425 MHz, which is clear evidence for parametric excitation. In particular, the slight increase in the frequency at maximum amplitude when the gap distance was increased confirms that the data shown in FIGS. 10 and 11 corresponds to a mechanical resonance of the cantilevered MWNT, since the increase in the measured resonant frequency can be traced to a decrease in the effective electrostatic forces. (As described by Sarid D. *Scanning Force Microscopy with applications to electric magnetic and atomic forces*" Oxford University Press: New York Oxford, 1991.) In addition, the phase change remains constant with increase in gap distance, as would be expected, and the quality factor Q decreased from 37 to 31 when the gap was increased.

The Young's modulus, Y, for the MWNT was also computed from the data using a multi-step procedure.

For a MWNT clamped at one end, the frequency of the $i^{th}$ mode of vibration is given by:

$$f_i = \frac{\beta_i^2}{8\pi} \frac{1}{L^2} \sqrt{\frac{(D_o^2 + D_i^2)Y}{\rho}},$$

where L is the tube length, $D_o$ and $D_i$ are the outer and inner tube diameters respectively. $\rho$ is the density of the MWNT and the $\beta_i$'s were determined from the boundary conditions to be $\beta_1=1.875$; $\beta_2=4.694$; $\beta_3=7.855$. According to the present invention, it is possible to measure the bending modulus of the nanotube. Moreover, as long as the nanotube does not change its geometry by buckling or any other such deformation, the bending modulus will be equal to the Young's modulus. (For additional discussion, see "Gaillard, J., Skove, M. J. & Rao, *App. Phys. Lett.* 86, 233109-233109-3 (2005)" previously incorporated herein by reference.) The geometric parameters for the MWNT investigated here were determined from SEM images to be: L=10 μm, $D_o$=57 nm and $D_i$=17 nm, as described above. In addition, the density of the MWNT was determined (via methods described by Lu Q.; Keskar G.; Ciocan R.; Larcom L. L.; Rao A. M NT05: *Sixth International Conference on the Science and Application of Nanotubes*, 2005, Gothenburg, Sweden 426, which is incorporated herein by reference) to be $\rho$=2100 Kg/M$^3$.

Figure 12:
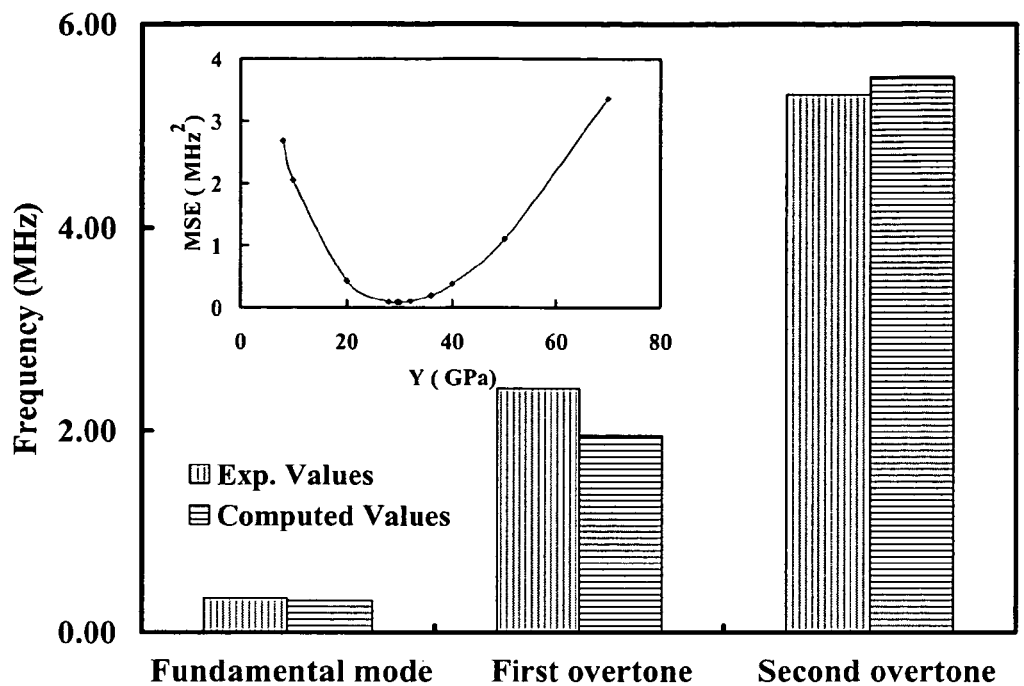
FIG. 12 illustrates the calculated fundamental, $1^{st}$, and $2^{nd}$ overtone modes for a system obtained from the multi-step Young's modulus calculations described in Example 5 and compares those results to the results obtained experimentally according to the presently disclosed process for the first three oscillation modes of a MWNT nano-cantilever.
Figure 13:
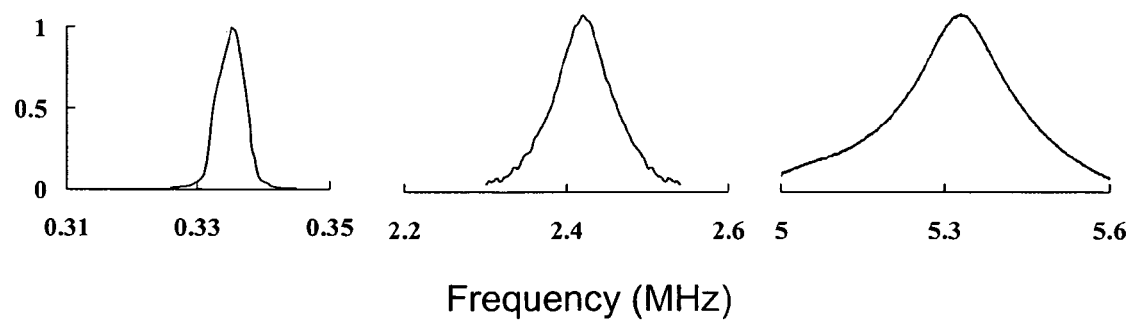
FIG. 13 graphically illustrates the measured amplitude for the fundamental, first, and second overtones in a system including a MWNT nano-cantilever.

The first three oscillation modes of the MWNT were identified from the amplitude and phase changes shown in FIGS. 10 and 11. The experimentally determined resonances were found at $f_{1e}$=0.339 MHz, $f_{2e}$=2.42 MHz and $f_{3e}$=5.31 MHz, as shown in FIGS. 12 and 13. At each step of the multi-stop procedure, the $f_i$'s were computed using the equation above starting with the measured values for $D_o$, $D_i$ and L and a range of values for Y. Then the mean squared error (MSE) for a particular Y was computed as:

$$MSE = \frac{1}{3}\sum_{i=1}^{3}(f_i - f_{ie})^2$$

Figure 14:
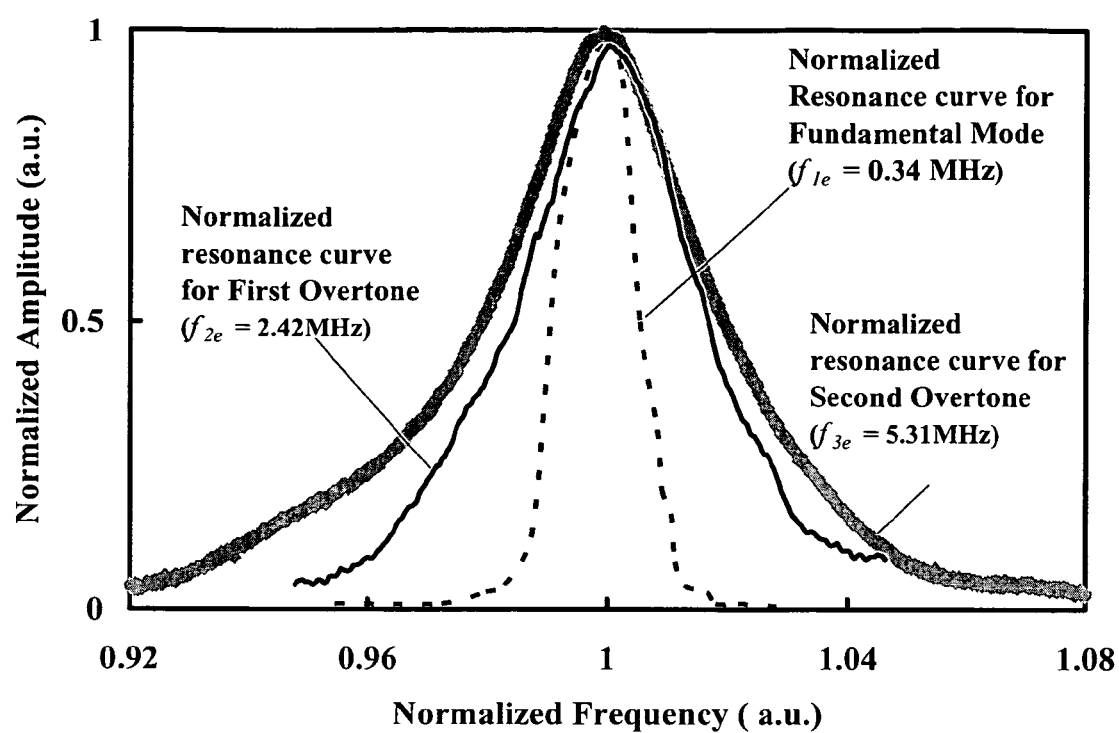
FIG. 14 illustrates the data of FIG. 13 on a normalized frequency scale.

As the inset in FIG. 12 shows, a minimum in MSE for Y=29.6 GPa was found. The values of L and $D_o$ were then perturbed by about ±10% and the minima in MSE recomputed to offer assurance that the minimum was global rather than local. A comparison between experimentally determined frequencies and computed values for Y=29.6 GPa is also shown in FIG. 12. The average error in frequency estimation was about ~10% (ranging from 18% for the first overtone to 3% for the second overtone). The determined value for the Young's modulus Y=29.6±2.9 GPa is in excellent agreement with those reported in the literature for MWNTs with comparable dimensions. The quality factor for each of the three resonances was determined to be 67, 36 and 25 for the fundamental and first two overtones respectively, as illustrated in FIG. 14.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention. Further, it is recognized that many embodiments may be conceived that do not achieve all of the advantages of some embodiments, yet the absence of a particular advantage shall not be construed to necessarily mean that such an embodiment is outside the scope of the present invention.

What is claimed is:

1. A method of detecting resonance in an element comprising:
    locating a counter electrode a predetermined distance from an element such that the element and the counter electrode are in a non-contact mode, wherein the element comprises a semi-conductive material or a carbon nanotube and has a length of less than about 500 μm and a width of less than about 50 μm;
    inducing an electrostatic force on the element by applying a first electric signal to the counter electrode;
    generating a second electric signal at the semi-conductive material or the carbon nanotube in direct response to the induced electrostatic force;
    directly examining the second electric signal and;
    ascertaining the presence of at least one subharmonic or superharmonic of the resonant frequency of the element in the second electric signal.

2. The method according to claim 1, wherein the element is a single-clamped or doubly clamped element.

3. The method according to claim 1, wherein the element comprises a carbon-based nano structure.

4. The method according to claim 1, wherein the amplitude of the second electric signal is examined to ascertain the presence of at least one subharmonic or superharmonic of the resonant frequency of the element.

5. The method according to claim 1, wherein the second electric signal is examined to ascertain the presence of the second harmonic of the resonant frequency of the element.

6. The method according to claim 1, wherein the second electric signal is examined to ascertain the presence of the third harmonic of the resonant frequency of the element.

7. The method according to claim 1, further comprising ascertaining the quality factor of the second electric signal.

8. The method according to claim 1, further comprising feeding the first electric signal and the second electric signal to a lock-in amplifier, wherein the second electric signal is examined at the lock-in amplifier.

9. The method according to claim 1, wherein the method is carried out at ambient conditions.

10. The method according to claim 1, wherein the first electric signal is a variable signal.

11. The method according to claim 1, further comprising interacting a chemical species with the element.

12. The method according to claim 11, wherein the interaction is adsorption of the species on to the element.

13. The method according to claim 12, further comprising locating a binding agent specific for the species on the surface of the element.

14. The method according to claim 11, further comprising subjecting the chemical species to an environmental condition, wherein the chemical species undergoes a characteristic change upon subjection to the environmental condition.

15. The method according to claim 11, wherein said interaction changes the resonant frequency of the element.

16. The method according to claim 1, wherein the phase of the second electric signal is examined to ascertain the presence of at least one subharmonic or superharmonic of the resonant frequency of the element.

17. An electrical device comprising:
an element having a length less than about 500 μm and a width less than about 50 μm, the element comprising a semi-conductive material or a carbon nanotube;
a counter electrode located a predetermined distance from the element such that the element and the counter electrode are in a non-contact mode;
a signal generator for applying a first electric signal to the counter electrode and inducing an electrostatic force on the element;
a signal processor for examining a second signal generated at the semi-conductive material or the carbon nanotube in direct response to the induced electrostatic force, wherein the signal processor directly examines the second signal to ascertain the presence of at least one subharmonic or superharmonic of the resonant frequency of the element in the second signal.

18. The electrical device of claim 17, wherein the signal processor is a lock-in amplifier.

19. The electrical device of claim 17, wherein the signal generator applies a modulated signal to the counter electrode.

20. The electrical device of claim 17, wherein the element and the counter electrode are in a parallel arrangement.

21. The electrical device of claim 20, wherein the predetermined distance is between about 1 μm and about 20 μm.

22. The electrical device of claim 20, wherein the element is less than about 500 nm in width.

23. The electrical device of claim 22, wherein the predetermined distance is between about 1 μm and about 2 μm.

24. The electrical device of claim 17, wherein the element and the counter electrode are in a tip-to-tip arrangement.

25. The electrical device of claim 17, wherein the element is a single-clamped cantilever.

26. The electrical device of claim 17, wherein the element is a double-clamped beam.

27. The electrical device of claim 17, wherein the element comprises a carbon-based nanostructure.

28. The electrical device of claim 17, further comprising a stage for location of a species.

29. The electrical device of claim 17, further comprising a fluid flow field that contacts a surface of the element.

30. The electrical device of claim 29, wherein the fluid flow field is for a gas or vapor fluid flow.

31. The electrical device of claim 17, wherein the device is a chemical sensor.

32. The electrical device of claim 17, wherein the device is an atomic force microscope.

33. The electrical device of claim 17, wherein the element comprises a non-conductive base substrate and a conductive or semi-conductive outer layer.

34. The electrical device of claim 28, wherein interaction of the species with the element alters the resonant frequency of the element.

* * * * *

UNITED STATES PATENT AND TRADEMARK OFFICE
CERTIFICATE OF CORRECTION

PATENT NO.         : 7,598,723 B2                                           Page 1 of 1
APPLICATION NO.    : 11/354268
DATED              : October 6, 2009
INVENTOR(S)        : Jay Gaillard et al.

It is certified that error appears in the above-identified patent and that said Letters Patent is hereby corrected as shown below:

In the Specification

Column 1, lines 17-18 - - please correct "...National Science Foundation Grant No. 2003863" to read "...National Science Foundation Grant No. DMR-0304019."

Signed and Sealed this
Second Day of June, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 7,598,723 B2 | Page 1 of 1 |
| APPLICATION NO. | : 11/354268 | |
| DATED | : October 6, 2009 | |
| INVENTOR(S) | : Jay Gaillard et al. | |

It is certified that error appears in the above-identified patent and that said Letters Patent is hereby corrected as shown below:

In the Specification

Column 1, lines 16-18, please correct -- "The United States Government may have rights in this invention pursuant to National Science Foundation Grant No. 2003863." -- to read -- "This invention was made with government support under NSF grant #DMR-0304019. The government has certain rights in the invention, 37 CFR 401.14(f)(4)." --

Signed and Sealed this
Twenty-fourth Day of November, 2015

Michelle K. Lee
*Director of the United States Patent and Trademark Office*